(12) United States Patent
Lee et al.

(10) Patent No.: US 7,318,819 B2
(45) Date of Patent: Jan. 15, 2008

(54) AUTOMATIC LOCKING VALVE FOR MEDICATION INJECTION

(75) Inventors: Young Gyu Lee, Seoul (KR); Ki Woon Kim, Gyunggi-Do (KR)

(73) Assignee: Woo Young Medical Co., Ltd, Gyoha Myun, Paju, Gyunggi-Do (KR)

( * ) Notice: Subject to any disclaimer, the term of this patent is extended or adjusted under 35 U.S.C. 154(b) by 0 days.

(21) Appl. No.: 10/913,878

(22) Filed: Aug. 5, 2004

(65) Prior Publication Data

US 2006/0030821 A1    Feb. 9, 2006

(51) Int. Cl.
*A61M 5/00*    (2006.01)
(52) U.S. Cl. ............... 604/187; 604/151; 604/408; 604/410; 604/503
(58) Field of Classification Search .......... 604/167.01, 604/246, 256, 284, 503; 600/488; 137/613
See application file for complete search history.

(56) References Cited

U.S. PATENT DOCUMENTS 4,078,562 A * 3/1978 Friedman .................. 604/503
4,304,260 A * 12/1981 Turner et al. ............... 137/613
4,739,770 A * 4/1988 Stephens et al. ............ 600/488
6,146,360 A * 11/2000 Rogers et al. .............. 604/151
6,863,083 B2 * 3/2005 Danby et al. ............... 137/384

* cited by examiner

*Primary Examiner*—Kevin C. Sirmons
*Assistant Examiner*—Phillip Gray
(74) *Attorney, Agent, or Firm*—GWiPS

(57) ABSTRACT

An automatic locking valve for safely administering a dose of medication is disclosed. The automatic locking valve comprises a valve housing defined with a space and formed with input and output ports for intaking and discharging the medication, a spool-shaped on/off member having a diameter smallest at the center thereof and being tapered to linearly increase toward upper and lower portions of the on/off member so that the on/off member moves up and down depending on a closed state of the door, and a membrane attached to the space of the valve housing such that the membrane expands toward a lower portion of the space due to an elasticity of the membrane when the tube is blocked. The medication can be safely and accurately administered under a condition of installation with the door closed above the tube.

4 Claims, 3 Drawing Sheets

AUTOMATIC LOCKING VALVE FOR MEDICATION INJECTION

BACKGROUND OF THE INVENTION

1. Field of the Invention

The present invention relates to an automatic locking valve for medication injection, and more particularly to an automatic locking valve for medication injection, which is provided with a blocking sensor for sensing blockage of a tube and with automatic locking means for performing an operation corresponding to a mounting state of a door such that a dose of medication can be administered only under an installation condition in which the door is completely-closed after the tube is installed, so that the dose of medication can be safely administered to a patient.

2. Description of the Related Art

As is well known in the prior art, in order to administer a dose of medication prescribed by a doctor to a patient, after the dose of medication is placed at a higher position than an injecting position at the patient, a valve with an on/off part of a torsional screw-like shape therein should be adjusted in accordance with the experience of a nurse performing injection of the predetermined dose to the patient.

When the patent is administered with the dose of medication, such as an analgesic, there often come intermittent convolutions or pains, forcing a temporary increase of the dose of injection. With regard to this, since the dose should be administered according to a prescription of the doctor, it is very dangerous for the patient to adjust his or her own dose of injection. However, under the present circumstances of hospitals, a prompt adjustment for the dose of injection corresponding to the intermittent pains of the patient is very difficult for medical staffs and causes very serious consumption of time for them.

For a nurse inexperienced in adjusting the dose of injection, it is very difficult to adjust a dose of injection an hour such that the prescribed dose is administered with accuracy. Further, in case of a patient with a special disease, such as acute cardiac paralysis, a requirement of being administered only when the patient suffers an attacks forces the patient to always carry the medication for the disease and a requirement of administrating an accurate dose of medication requires great deal of skill in administration.

Even for an expert in administration, there is always a danger of unintentional excessive administration of the medication. Further, when extraneous substances or air are contained in the medication or when something presses a tube, it poses a serious threat to the patient.

Although an automatic injector for automatically injecting a predetermined dose of medication has been recently developed, it simply adopts a compulsory injection system for injecting the medication using a water pump and does not have separate sensors for sensing the dose injected, thereby causing a very high possibility of safety accident. Further, when a door is being opened, an excessive dose of medication can be injected at one time, resulting in potentially life-threatening situation.

SUMMARY OF THE INVENTION

The present invention has been made to solve the above problems, and it is an object of the present invention to provide an automatic locking valve for medication injection, which is provided with a blocking sensor for sensing blockage of a tube and with automatic locking means for performing an operation corresponding to a mounting state of a door such that a dose of medication can be administered only under an installation condition in which the door is completely closed after the tube is installed, so that the dose of medication can be safely administered to a patient.

In accordance with an aspect of the present invention, the above and other objects can be accomplished by the provision of an automatic locking valve, being installed in the automatic dose administrating apparatus comprising: a housing for supporting outer portions of three compartments divided in the housing; a medication container for storing a medication pack therein, the medication container defined at the uppermost part of the housing; a ball-loose switch for generating a command signal of medication injection via an electric line, the ball-loose switch being provided at a predetermined part of an outer side of the housing; a driving room for controlling injection state of the medication, the driving room being provided with a pressure pump for driving discharge of the medication by pumping the medication; and a tube for transferring the medication discharged from the medication pack to a needle, the tube extending from an inner part of the driving room to an outer part thereof and the medication being discharged through the tube after being pumped by the pressure pump, wherein the automatic locking valve is received in the driving room such that the automatic locking valve is connected, at one side, to the tube connected to the medication pack and is connected, at the other side, to the tube connected to the needle, such that the automatic locking valve controls flow of the medication therein depending on a closed state of a door of the driving room.

Preferably, the automatic locking valve comprises: a valve housing for defining a space therein, the valve housing having input and output ports for allowing the medication to flow in and out; an on/off member of a spool-like shape, the on/off member having a diameter smallest at the center thereof and being tapered to linearly increase toward upper and lower portions of the on/off member so that the on/off valve moves up and down depending on the closed state of the door; and a membrane attached to the space of the valve housing such that the membrane expands toward a lower portion of the space due to elastic properties of the membrane when the tube is blocked.

More preferably, the space of the valve housing has a shape tapered for a diameter of the space to increase from the center to an upper portion and to increase from the center to a lower portion in order to correspond to the shape of the on/off member; and the lower portion of the space has an increased inner diameter, so that when the on/off member is pressed down, the on/off member defines a fluid gap along with an inner circumferential surface of the valve housing.

Preferably, the valve housing further comprises a blocking sensor for generating a "High" signal with liquid or metal at a predetermined portion of the membrane and for sensing blockage of the tube when the membrane swells to expand toward the blocking sensor.

BRIEF DESCRIPTION OF THE DRAWINGS

The foregoing and other objects and features of the present invention will be more clearly understood from the following detailed description taken in conjunction with the accompanying drawings, in which.

DESCRIPTION OF THE PREFERRED EMBODIMENTS

Preferred embodiments of the present invention will now be described in detail with reference to the accompanying drawings.

Figure 1A:
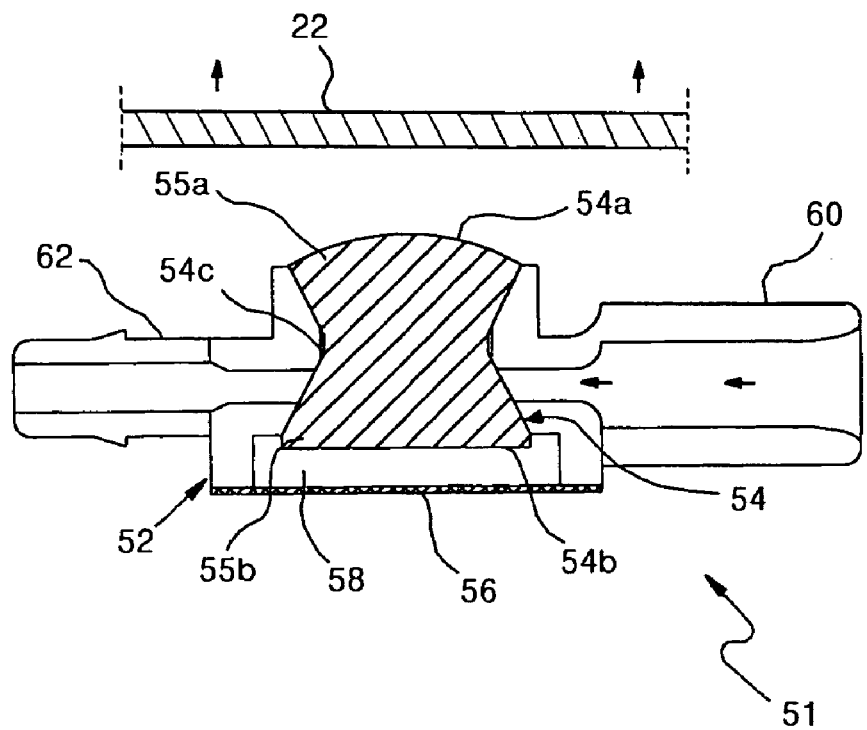
FIGS. 1a and 1b are side sectional views showing construction and operation of an automatic locking valve for medication injection in accordance with an embodiment of the present invention.
Figure 1B:
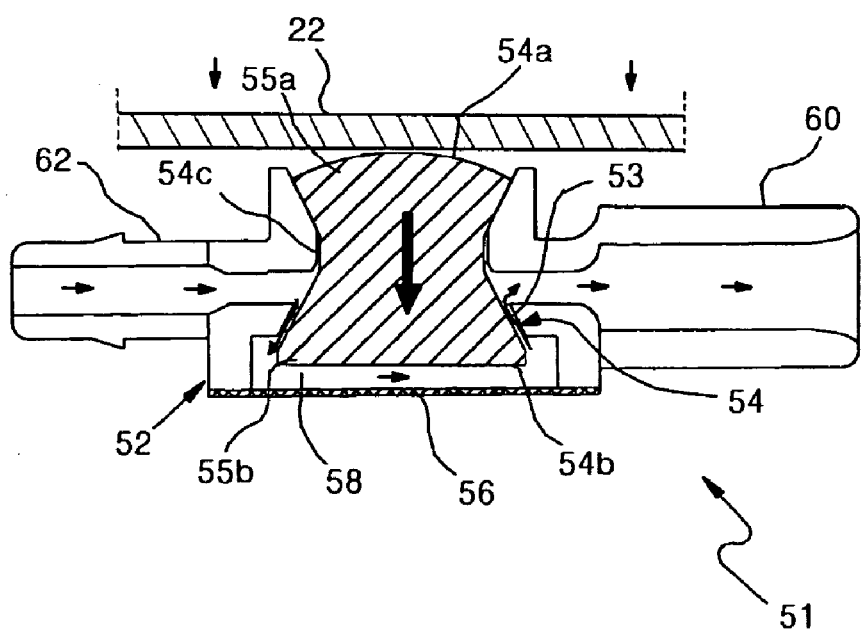

FIGS. 1a and 1b are side sectional views showing construction and operation of an automatic locking valve for medication injection in accordance with an embodiment of the present invention.

An automatic locking valve for medication injection 51 in accordance with the embodiment of the present invention is provided with a blocking sensor for sensing blockage of a tube and with automatic locking means for performing an operation corresponding to a mounting state of a door such that a dose of medication can be administered only under an installation condition in which the door is completely closed after the tube is installed, so that a patient can safely administer the dose of medication for oneself.

The automatic locking valve 51 of the present invention comprises a valve housing 52, which defines a space 58 therein and has input and output ports 60 and 62 connected with a tube (not shown), respectively, for allowing the medication to flow in and out.

The valve housing 52 defines the space 58 therein for receiving an on/off member 54 therein. The space 58 has a shape tapered for a diameter of the space to increase from the center to an upper portion and to increase from the center to a lower portion in order to correspond to the shape of the on/off member 54.

The on/off member 54 generally has a cylindrical shape. Specifically, like a spool, the on/off member 54 has a diameter smallest at the center thereof and tapered for the diameter of the on/off member to linearly increase toward upper and lower portions thereof, respectively. Here, the upper portion of the on/off member 54 acts as an on/off operation portion 55a and the lower portion thereof acts as an on/off portion 55b for controlling the medication directly flowing through the valve.

Specifically, with a cross-section of a circular shape in the horizontal plane, the on/off member 54 has an outer diameter increased from the center to the upper and lower portions, respectively, thereby forming the spool-like shape. The on/off member 54 has the top portion 54a curved convexly at the center thereof and the bottom portion 54b flattened to be parallel with the ground.

The on/off member 54 is elastic. Thus, when the on/off member 54 is pushed into the space defined by the upper portion-of the valve housing 52, the bottom portion and the outer circumferential portion thereof are compressed inwardly toward the inner center of the on/off member 54, so that it is gradually pushed into the space 58 of the valve housing 52, whereby the on/off member 54 is finally engaged with the valve housing 52.

When the on/off member 54 is installed in the valve housing 52, the flow of the medication through the space 58 of the valve housing 52 is controlled by the inlet and outlet ports 60 and 62, depending on pressure to be applied to the top surface of the on/off member 54. Specifically, with the on/off member 54 installed in the valve housing 52, the on/off member moves up and down inside the valve housing 62 by a predetermined distance. Thus, when the on/off operation member 55a of the on/off member 54 maintains close contact with the inner circumferential surface of the valve housing 52, there is no fluid gap allowing the medication to flow between them. However, when the on/off portion 55b at the lower portion thereof defines a fluid gap 53 along with the inner circumferential surface of the valve housing 52, the medication can flow into the lower portion of the space 58 through the fluid gap 53.

Thus, depending on whether the on/off member 54 is pushed down or not, the medication passed through the outlet port 60 flows or does not flows toward the inlet port 62 through the space 58.

Specifically, if the on/off member 54 is pushed down, as shown in FIG. 1b, the fluid gap 53 is opened so that the medication passing through the outlet port 60 can flow out via the space 58. If the on/off member 54 is not pushed down, as shown in FIG. 1a, the fluid gap 53 is closed so that the medication passing through the outlet port 60 cannot flow out because the medication passing through the outlet port 60 cannot flow into the space 58.

Figure 2:
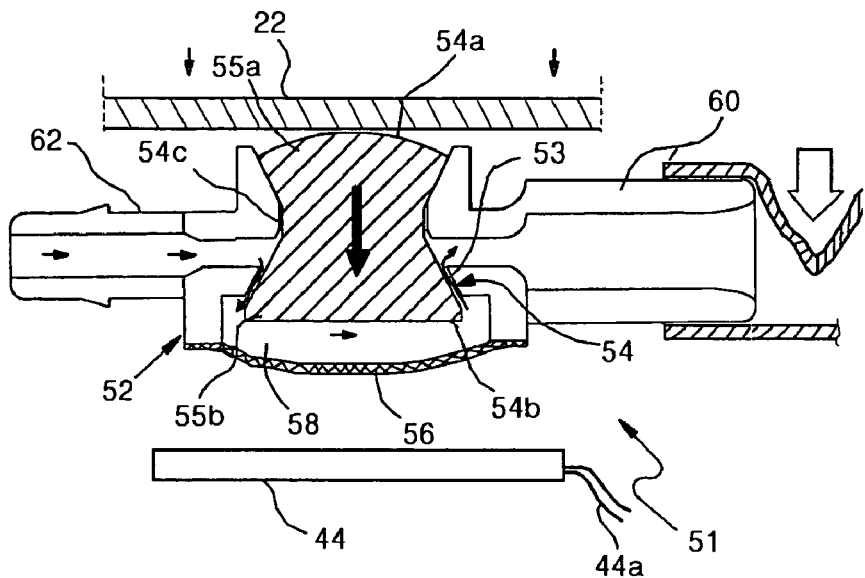
FIG. 2 is a side sectional view showing operation of a membrane provided in the automatic locking valve for injecting a dose of medication in accordance with the embodiment of the present invention.

FIG. 2 is a side sectional view showing operation of a membrane provided in the automatic locking valve for injecting a dose of medication in accordance with the embodiment of the present invention.

Referring to FIG. 2, the automatic locking valve 51 of the invention further comprises a membrane 56 at the lower portion of the space 58, of which the periphery is attached around the edge of a lower surface of the space 58 defined by the membrane 56.

The membrane 56 is made of a fine film and in spite of being elastic, does not expand when the medication flows. When the middle of a valve (not shown) connected with the inlet port 62 is folded or pressed down by something so that the medication cannot normally flow through the valve, the membrane 56 expands convexly in the direction of the lower portion for the pressure of accumulated medication in the space 58.

Further, as shown in FIG. 2, the membrane 56 is provided with, at its predetermined lower portion, a blocking sensor 44 for generating a "High" signal with liquid or metal. Thus, when the medication does not regularly flow, for example, due to the tube being pressed down on by something, the membrane 56 swells to expand toward the blocking sensor 44, thereby sensing the blockage of the tube.

Figure 3:
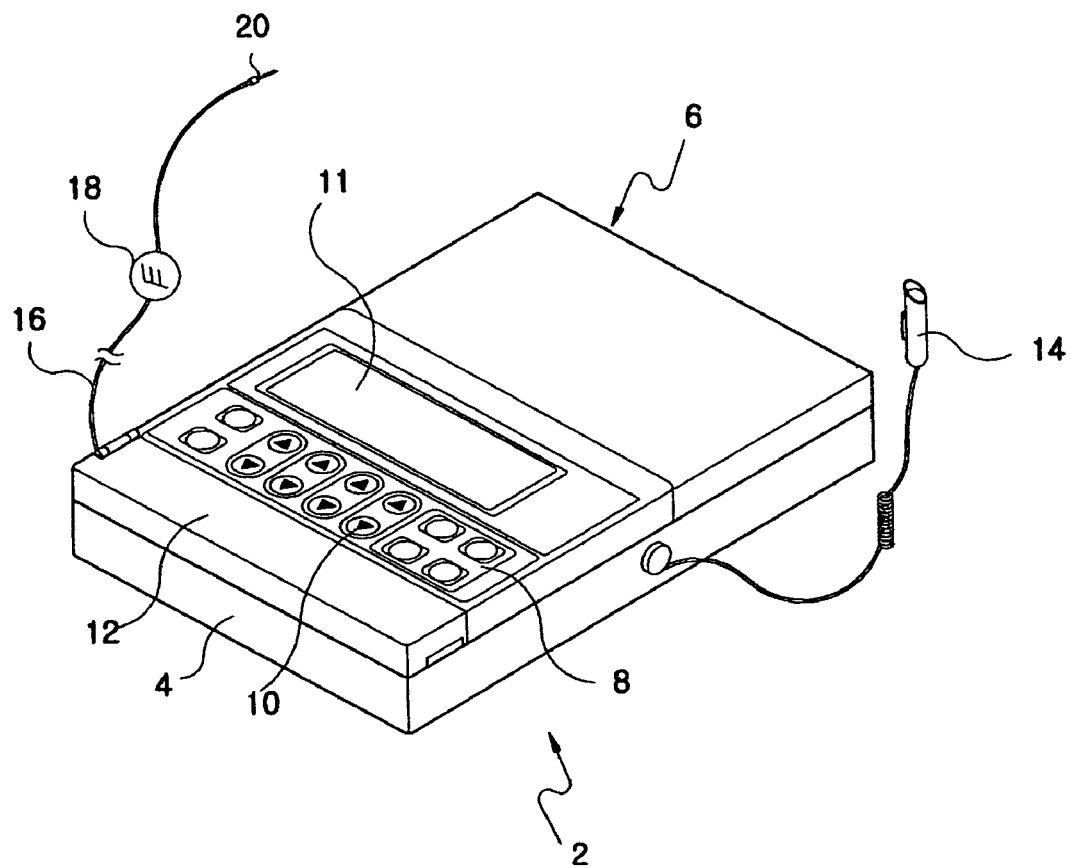
FIG. 3 is a perspective view of an appearance of an automatic dose administrating apparatus in accordance with an embodiment of the present invention.

FIG. 3 is a perspective view of an appearance of an automatic dose administrating apparatus applied with the automatic locking valve 51 for medication injection according to the embodiment of the present invention.

Referring to FIG. 3, the automatic dose administrating apparatus 2 according to an embodiment of the present invention is provided with the automatic locking valve for sensing a mounting state of a door and a blocking sensor for sensing blockage of a tube, such that the dose of medication can be administered under a condition of completed installation with the door closed above the tube mounted in the apparatus, whereby a patient can safely administer his or her own dose of medication.

The automatic lock valve for medication administration of the invention can be applied to the automatic dose administrating apparatus 2, as shown in FIG. 3. The automatic dose administrating apparatus 2 is provided with a housing 4 divided into three compartments. Among the compartments, the uppermost compartment defines a medication storage chamber 6 storing a medication pack therein, and the middle compartment defines a control chamber 8 having an LCD 11 for displaying the installation state.

Under the control chamber 8, the lowermost compartment defines a driving room 12 for controlling injection of the medication while driving a discharge of the medication through tube 16 by pumping the medication.

As the housing 4 is provided with a ball-loose switch 14 at a predetermined part of the side thereof, the user can temporarily increases the dose of injection by operating the ball-loose switch 14. The tube 16 is provided with a needle 20 at one end thereof and also provided with an air-filter 18 at the middle of the tube 16 extending from the housing 4 to the needle 20. The air-filter 20 discharges air contained in the medication flowing through the tube 16 after filtering air. The control part 8 is provided with a button part 10 on the surface thereof, which can set a various settings by operation of its keys.

Using the automatic dose administrating apparatus 2 installed with the sensors as described above, the patient can be very conveniently administered with a predetermined dose of medication without any restriction by time or place while always carrying it. Further, due to the sensor being organically associated with each other to ensure safety of the patient during administration, the patient can control the administration of the medication and does not need an additional nurse in a daily life.

Figure 4:
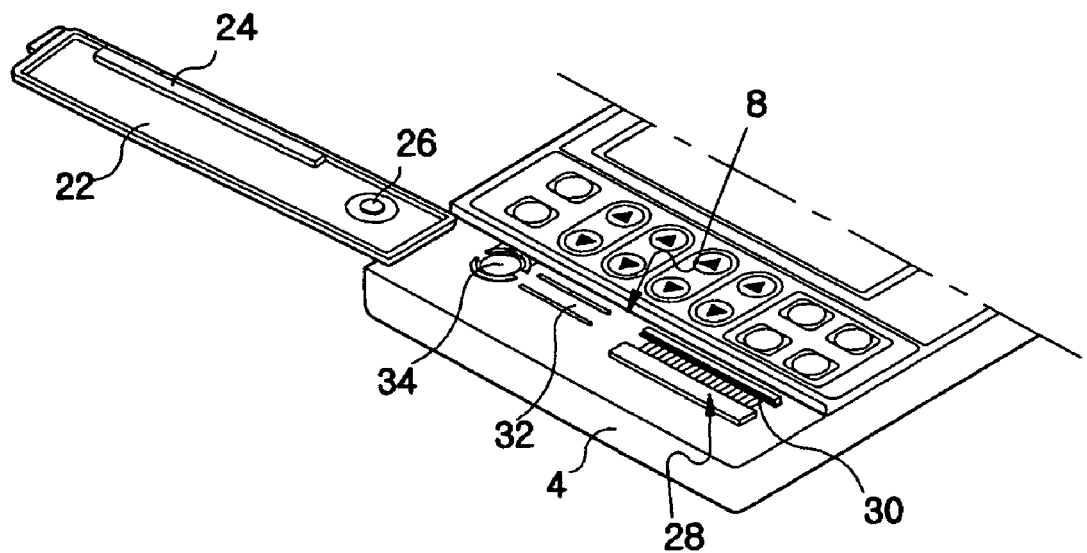
FIG. 4 is a partial perspective view showing, in detail, the construction of the automatic dose administrating apparatus with the automatic locking valve 51 of the present invention applied to it.

FIG. 4 is a partial perspective view showing in detail the construction of the automatic dose administrating apparatus with the automatic locking valve 51 for medication injection according to the embodiment of the present invention applied to it.

Referring to FIG. 4, at lowermost portion of the housing 4, the automatic dose administrating apparatus 2 is provided with the driving room 12 for generating driving force to inject the medication with an application of a signal for controlling the injection of the medication. The driving room 12 is provided with a door 22 hinged at the top of the driving room 12. At the bottom of the door 22, the door 22 is provided with a supporting bar 24 for pressing the tube 16 and with a pressing protrusion 26 for making a press in order to maintain a check valve of the tube 16 in an open state.

The driving room 12 is provided with a pressure pump 28 therein, comprising a motor (not shown) for generating a rotational driving force of a predetermined revolutions per minute with an electric control and a plurality of longitudinally connected pressing pieces 30 which move up and down with supply of the rotational driving force.

The pressing piece 30 sinusoidally moves up and down by a rotational force of a cam (not shown). Thus, the pressing piece 30 presses the bottom of a main tube (not shown) to the sinuous shape, causing the medication in the tube 16 to flow in one direction.

On the top of the housing 4 to which the door 22 of the driving room 12 is connected, the housing 4 is formed with a guiding groove 32 for guiding the tube 16 in the state of mounting the tube 16 in the housing, and with a check valve receiving groove 34 at the side of the guiding groove 32.

If the door 22 is closed after the automatic locking valve 51 is inserted into the driving room with the medication pack (not shown) received in the medication storage chamber 6, the bottom of the door 12 presses the on/off member 54 of the automatic locking valve 51, generating a flow passage of the medication with the fluid gap opened. Meanwhile, if the door 22 is opened, the on/off member 54 returns back to the upper portion thereof due to elasticity, closing the flow passage of the medication with the fluid gap closed. Further, if the medication does not regularly flow, for example, due to the tube pressed by something in the middle thereof, the membrane 56 swells to expand toward the blocking sensor 44, so that the blocking sensor 44 can sense the blockage of the tube, whereby the patient can be safely administered with medication for himself or herself.

Figure 5:
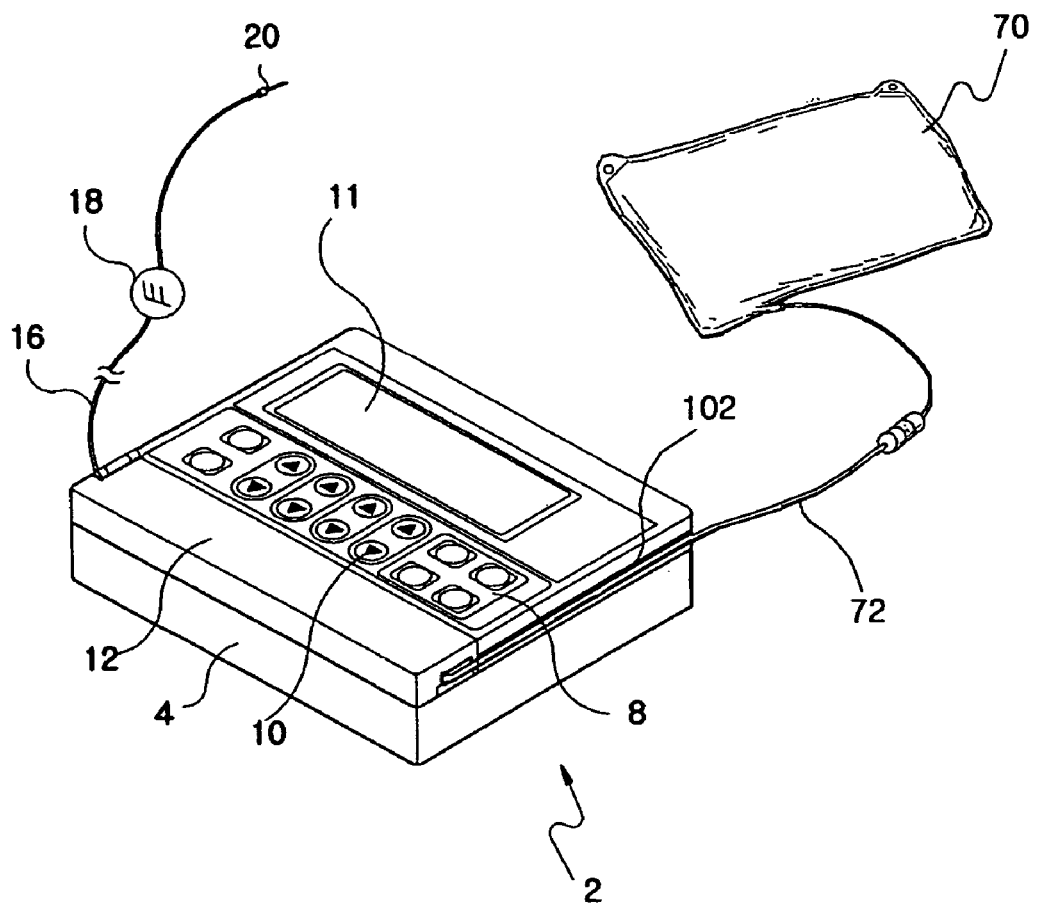
FIG. 5 is a perspective view of an automatic dose administrating apparatus according to another embodiment of the present invention.

FIG. 5 is a perspective view of an automatic dose administrating apparatus according to another embodiment of the present invention, in which similar components to those of the automatic dose administrating apparatus of FIG. 3 are indicated by the same reference numerals as those of FIG. 3.

Referring to FIG. 5, an automatic dose administrating apparatus 2 with the automatic locking valve 51 for medication injection of the present invention applied to it may be provided with a connecting tube 72 directly connected to a special medication pack 70, instead of the medication storage chamber 6 as shown in FIG. 3.

In this case, the housing 4 of the automatic dose administrating apparatus 2 is preferably provided with a slot 102 at an outer side thereof in the lengthwise direction for leading the connecting tube 72. Thus, regardless of the type of medication pack, the medication pack 70 can be connected to the automatic dose administrating apparatus 2 using the connecting tube 72, and a predetermined dose of medication can be administered to the patient from the inside of the automatic dose administrating apparatus 2.

As is apparent from the description, in accordance with the present invention, the automatic locking valve for medication injection is provided with an automatic locking valve for sensing a mounting state of a door and a blocking sensor for sensing blockage of a tube, such that a dose of medication can be administered under a condition of completed installation with the door closed above the tube mounted in the automatic locking valve, thereby providing safety and accuracy when administering the dose to a patient.

It should be understood that the embodiments and the accompanying drawings as described above have been described for illustrative purposes and the present invention is limited by the following claims. Further, those skilled in the art will appreciate that various modifications, additions and substitutions are allowed without departing from the scope and spirit of the invention as set forth in the accompanying claims.

What is claimed is:

1. An apparatus for automatically administrating dose of medication consists of an automatic operating member, the apparatus comprising:

a case (4) divided into three compartments, a medication storage chamber (6) for storing a medication pack, a control chamber (8) equipped an LCD (11), and a driving chamber (12) to control injecting the medication, said driving chamber (12) providing a pressure pump (28) for supplying the medication, and a tube (16) for transferring the medication from the medication pack to a needle (20), said tube (16) extended from inner driving chamber (12) to outer case (4), and a lid (22) having a bar (24) for supporting said tube (16) and a pressure protrusion (26), a ball-loose switch (14) for issuing a command signal via an electric line to inject the medication, said ball-loose switch (14) positioned at a predetermined distance outside of the case (4), an automatic locking valve (51) consisting of a valve housing (52), an input port (60) and an output port (62) for flowing the medication, wherein said valve housing (52) formed three parts of inner cavities and an outer cavity, which are a funnel-shaped inner cavity at top portion, an upside-down funnel-shaped inner cavity at lower portion, a disk-shaped inner cavity at middle portion for connecting between the top and lower inner cavity portions and an upside down Petri-dish shaped outer cavity at bottom portion, an on-off member (54) having a slimmed center (54c), wider diameters at top (54a) and bottom (54b) surface and tapered linearly from center to the top and bottom surface to form a concaved lateral surface, so that said on-off member (54) forming the funnel-shaped upper portion, the upside-down funnel-shaped lower portion, and the disk-shaped neck middle portion for suitably fitting into the inner cavities of said valve housing (52) is pushed down as closing said lid (22) to have a lateral clearance as a flow path of the medication and lifted up to block the lateral clearance as opening said lid (22), a membrane (56) attached around a rim of the upside down Petri-dish shaped bottom portion of said valve housing (52) for providing a cavity (58) below the bottom of said on-off member (54b) as the flow path of the medication, said membrane (56) expanding outward when the tube (16) is blocked by a foreign object, and a sensor (44) for detecting a status of blocking the tube (16) to issue a "high signal" when said membrane (56) is swollen to contact said sensor (44).

2. An apparatus for automatically administrating dose of medication as set forth in claim 1, wherein said on-off member has a convex top surface to be easily pushed down by the lid (22) when the lid (22) is closed.

3. An apparatus for automatically administrating dose of medication as set forth in claim 1, wherein said on-off member (54) has a flat bottom surface to provide said cavity (58) between said membrane (56) as a flow path of the medication.

4. An apparatus for automatically administrating dose of medication as set forth in claim 1, wherein said valve housing (52) forms trapezoidal cross section of a valve mounting seat for circumferentially contacting to the tapered lateral surface of said on-off member (54).

* * * * *